United States Patent [19]

Karn

[11] 4,266,945

[45] May 12, 1981

[54] MOLYBDENUM-CONTAINING COMPOSITIONS AND LUBRICANTS AND FUELS CONTAINING THEM

[75] Inventor: Jack L. Karn, Richmond Heights, Ohio

[73] Assignee: The Lubrizol Corporation, Wickliffe, Ohio

[21] Appl. No.: 96,876

[22] Filed: Nov. 23, 1979

[51] Int. Cl.$^3$ .................. A01M 23/00; A01M 23/16
[52] U.S. Cl. .................. 44/68; 252/49.7; 260/429 R
[58] Field of Search .................. 252/49.7; 44/68; 260/429 R

[56] References Cited

U.S. PATENT DOCUMENTS

| | | | |
|---|---|---|---|
| 3,282,838 | 11/1966 | Knowles et al. | 252/49.7 |
| 3,290,245 | 12/1966 | Elliott et al. | 252/49.7 |
| 3,398,170 | 8/1968 | Cyba | 44/68 X |
| 3,453,212 | 7/1969 | Dorer | 252/49.7 |
| 3,493,508 | 2/1970 | Andress | 252/49.7 X |
| 3,557,171 | 1/1971 | Andress | 252/49.7 |
| 4,164,473 | 8/1979 | Coupland et al. | 252/32.7 E |
| 4,176,073 | 11/1979 | Ryer et al. | 252/49.7 X |
| 4,176,074 | 11/1979 | Coupland et al. | 252/49.7 X |
| 4,201,683 | 5/1980 | Brewster | 252/49.7 X |

*Primary Examiner*—Helen M. S. Sneed
*Attorney, Agent, or Firm*—Daniel N. Hall; William H. Pittman; Raymond F. Keller

[57] ABSTRACT

Molybdenum-containing compositions are prepared by the reaction of an acid of molybdenum or salt thereof, phenol or aldehyde condensation product therewith, and a primary or secondary amine. The preferred amines are diamines such as tallow-substituted trimethylene diamine and their formaldehyde condensation products. An optional but preferred ingredient in the reaction mixture is at least one oil-soluble dispersant. The molybdenum-containing compositions are useful as additives in lubricants and fuels, and are especially useful in lubricants when combined with compounds containing active sulfur.

21 Claims, No Drawings

MOLYBDENUM-CONTAINING COMPOSITIONS AND LUBRICANTS AND FUELS CONTAINING THEM

This invention relates to new molybdenum-containing compositions of matter, methods for their preparation, and their use as extreme pressure and friction modifying additives in lubricants and fuels. In its broadest aspect, the invention is directed to molybdenum-containing compositions substantially free of Group IA and IIA metals which are prepared by reacting, at a temperature up to about 200° C., a mixture comprising (A) at least one acid of molybdenum, or salt thereof; (B) at least one phenol, or condensation product of said phenol and at least one lower aldehyde; and (C) at least one compound selected from the group consisting of (1) amines having the formula

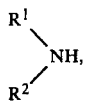

wherein $R^1$ is an aliphatic hydrocarbon-based radical and $R^2$ is hydrogen or an aliphatic hydrocarbon-based radical; (2) condensation products of said amines with at least one lower aldehyde; and (3) salts of (1) or (2).

It is known to prepare molybdenum-containing compositions useful as lubricant additives by the reaction of an inorganic molybdenum compound with an oil-soluble basic alkaline earth metal compound; reference is made, for example, to U.S. Pat. Nos. 3,453,212 and 3,541,014. It is of interest, however, to develop methods for reliably increasing the amount of molybdenum which can be incorporated in compositions useful as lubricant and fuel additives. The presence of alkaline earth metals in the compositions of the prior art frequently causes rather wide variation in the amount of molybdenum which can be stably incorporated therein.

A principal object of the present invention, therefore, is to prepare molybdenum-containing compositions useful as additives for lubricants and fuels.

A further object is to provide a method by which relatively large and substantially consistent proportions of molybdenum can be stably incorporated in lubricant and fuel additive compositions.

A further object is to prepare additives capable of improving extreme pressure properties and frictional characteristics of lubricants and fuels.

Other objects will in part be obvious and will in part appear hereinafter.

As will be apparent from the summary of the invention hereinabove, the compositions of this invention are prepared from a mixture comprising three essential reactants. Reagent A is at least one acid of molybdenum or salt thereof, most often one in which the molybdenum is hexavalent. Illustrative acids are active forms of molybdic acid ($H_2MoO_4$) and the isopolymolybdic acids including $H_2Mo_2O_7$, $H_3Mo_3O_{10}$, $H_2Mo_6O_{19}$, $H_6Mo_7O_{24}$, $H_2Mo_8O_{25}$ and $H_4Mo_8O_{26}$. Also suitable are active forms of the heteropoly acids of molybdenum, which contain a plurality of molybdenum atoms surrounding one or more central atoms which may be phosphorus, silicon, tin, arsenic, titanium, cerium, nickel, manganese, copper or the like. It is also within the scope of the invention to use heteropoly acids in which some of the molybdenum atoms are replaced by atoms of other metals such as tungsten.

The salts of the molybdenum acids are preferred for use as reagent A, especially the ammonium and alkali metal salts.

A large number of suitable molybdenum acid salts is disclosed in Kirk-Othmer, *Encyclopedia of Chemical Technology*, Second Edition, Vol. 13, pp. 649–652, which is incorporated by reference herein. An especially preferred molybdenum salt is ammonium paramolybdate, which may be represented by the formula $(NH_4)_6Mo_7O_{24}.4H_2O$.

The equivalent weight of reagent A, for the purposes of this invention, is its molecular weight divided by the total cation (e.g., ammonium) valencies per molecule.

Reagent B may be at least one phenol; that is, at least one compound containing a hydroxy radical bound directly to an aromatic ring. The term "phenol" as used herein includes compounds having more than one hydroxy group bound to an aromatic ring, such as catechol, resorcinol and hydroquinone. It also includes alkyl phenols such as the cresols and ethylphenols, and alkenyl phenols. Preferred are phenols containing at least one alkyl substituent containing about 3–100 and especially about 6–20 carbon atoms, such as heptylphenol, octylphenol, dodecylphenol, tetrapropenealkylated phenol and octadecylphenol. Phenols containing more than one alkyl substituent may also be used, but the monoalkylphenols are preferred because of their availability and ease of production. The equivalent weight of the phenol is its molecular weight divided by the number of hydroxy groups per molecule.

Reagent B may also be a condensation product of one of the above-described phenols with at least one lower aldehyde, the term "lower" denoting aldehydes containing not more than 7 carbon atoms. Suitable aldehydes include formaldehyde, acetaldehyde, propionaldehyde, the butyraldehydes, the valeraldehydes and benzaldehyde. Also suitable are aldehyde-yielding reagents such as paraformaldehyde, trioxane, methylol, Methyl Formcel and paraldehyde. Formaldehyde and the formaldehyde-yielding reagents are especially preferred.

Reagent C, as is apparent from the formula, may be an aliphatic amine containing at least one primary or secondary amino group. The organic radicals attached to the amino group are aliphatic hydrocarbon-based radicals.

The term "hydrocarbon-based radical" as used herein denotes a radical having a carbon atom directly attached to the remainder of the molecule and having predominantly hydrocarbon character within the context of this invention. Such radicals include the following:

(1) Hydrocarbon radicals; that is, aliphatic (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like. Such radicals are known to those skilled in the art; examples include methyl, ethyl, propyl, butyl, hexyl, octyl, decyl, dodecyl, octadecyl, allyl, butenyl, dodecenyl, octadecenyl, cyclohexyl, phenyl, etc. (all isomers being included).

(2) Substituted hydrocarbon radicals; that is, radicals containing non-hydrocarbon substituents which, in the context of this invention, do not alter the predominantly hydrocarbon character of the radical. Those skilled in the the art will be aware of suitable substituents (e.g., halo, nitro, hydroxy, alkoxy, alkylthio, carbalkoxy, nitrile).

(3) Hetero radicals; that is, radicals which, while predominantly hydrocarbon in character within the context of this invention, contain atoms other than carbon present in a chain otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based radical.

Preferably, the hydrocarbon-based radicals in the reagents used according to this invention are free from acetylenic and often also from ethylenic unsaturation. The $R^1$ radical in component C is most often an aliphatic hydrocarbon-based radical having about 6–30 carbon atoms. $R^2$ may also be an aliphatic hydrocarbon-based radical, and if so it usually contains about 1–30 carbon atoms. Preferably, however, $R^2$ is hydrogen.

The amines may be monoamines or polyamines. Illustrative monoamines are methylamine, ethylamine, diethylamine, hexylamine, octylamine, dodecylamine and didodecylamine (all isomers being included), as well as ether amines prepared by cyanoethylation of an alcohol followed by reduction of the cyano group. The polyamines are preferred, and suitable polyamines include the ethylene polyamines; aminoalkyl-substituted imidazolines and piperazines; polyamines prepared by cyanoethylation of such materials as ammonia, alkylene polyamines, alkanolamines, aliphatic or alicyclic ketones, polyhydric alcohols, or heterocyclic amines followed by reduction (e.g., hydrogenation) of the cyano groups; and homologs of the foregoing in which one or more hydrogen atoms bound to amino nitrogen are replaced by methyl groups, with the proviso that at least one amino group is primary or secondary.

The especially preferred polyamines are diamines having the formula $R^3NH$—$R^4$—$NH_2$. In these diamines, $R^3$ is an aliphatic hydrocarbon radical having at least about 6 and usually about 6–20 carbon atoms, and $R^4$ is a divalent aliphatic hydrocarbon radical having about 2–8 and preferably about 2–6 carbon atoms and is usually a $C_{2-4}$ alkylene radical. Examples of especially preferred diamines of this type are those sold under the trademark "Duomeen". In these diamines, $R^3$ contains 16–18 carbon atoms and may be, for example, oleyl ("Duomeen O") or radicals derived from tallow fatty acids ("Duomeen T"), coconut fatty acids ("Duomeen C") or soya fatty acids ("Duomeen S"); and $R^4$ is the trimethylene radical.

Component C may also be a condensation product of at least one amine as described hereinabove with at least one of the lower aldehydes previously described with reference to reagent B. The use of amine-aldehyde (especially formaldehyde or a formaldehyde-yielding reagent) condensation products as reagent C is preferred, but is usually unnecessary when reagent B is a phenol-aldehyde condensation product.

Amine-aldehyde condensates useful as reagent C may be prepared by reacting the aldehyde with the amine in any convenient mole ratio, preferably about 0.5–2.0 moles of amine per mole of aldehyde. The reaction is carried out at a temperature high enough to remove water but not so high as to degrade the product and is continued at least until the product is substantially completely dehydrated. The preferred temperature is about 80°–210° C., especially 88°–163° C. The condensation may be effected in the presence of a basic catalyst, typically an alkaline earth metal oxide or hydroxide such as calcium or barium oxide or hydroxide, but such catalyst is not necessary and it is frequently preferred that the reaction be carried out in the absence thereof.

U.S. Pat. No. 3,053,645 is incorporated by reference herein for its disclosure of amine-aldehyde condensation products useful as reagent C. The preparation of similar condensation products, also useful as reagent C, is illustrated by the following examples.

EXAMPLE 1

A mixture of 100 parts of "Duomeen T", 3.2 parts of lime, 14.3 parts of water, 30.3 parts of paraformaldehyde and 49 parts of mineral oil is heated at 99°–105° C. until substantially all water is driven off. It is then cooled and filtered; the filtrate is a 70% solution in oil of the desired condensation product.

EXAMPLE 2

A mixture of 100 parts of "Duomeen T", 14.1 parts of water and 30.2 parts of paraformaldehyde is heated under reflux as water is removed by distillation. When no more water is evolved, the temperature is increased to 148° C. and the mixture is blown with nitrogen until all water has been removed. The condensation product is then cooled and filtered.

EXAMPLE 3

"Duomeen T", 4030 parts, is heated to 45° C. and 2604 parts of isobutyraldehyde is added at 50°–65° C. over 5½ hours. The mixture is heated as water is removed by distillation and heating is continued until substantially all the water has been removed (about 15½ hours). Excess isobutyraldehyde is then distilled by heating to a maximum temperature of 170° C. Upon cooling and filtering, the desired condensation product is obtained.

EXAMPLE 4

Following the procedure of Example 2, a condensation product is prepared from 716 parts (2 moles) of "Duomeen S", 208 parts (6.3 moles) of paraformaldehyde and 107 parts of water.

Reagent C can also be a salt of one of the amines or condensation products previously described. The anion of the salt is preferably a mineral acid anion such as chloride, bromide, or sulfate, although it may also be derived from an organic acid such as acetic or propionic acid.

The equivalent weight of reagent C is its molecular weight divided by the number of basic nitrogen atoms per molecule, adjusted if necessary to compensate for diluent.

The molybdenum-containing compositions of this invention may be prepared by merely blending the above-described reagents, a small amount of water, and, if desired, a substantially inert, normally liquid organic diluent such as benzene, toluene, xylene, petroleum naptha, mineral oil, ethylene glycol monomethyl ether or the like and heating to a temperature within the range of 80°–200° C., preferably about 90°–150° C., until reaction is substantially complete. After completion of the reaction, volatile materials are ordinarily removed by vacuum stripping, blowing with an inert gas or the like and the composition is filtered.

It is within the scope of the invention to prepare amine-aldehyde reaction products useful as reagent C in situ by the reaction of an amine with an aldehyde or aldehyde-yielding reagent (preferably formaldehyde or a formaldehyde-yielding reagent) in the presence of other reagents. Such a procedure is often preferred; for example, products containing a relatively large amount of molybdenum and having particularly favorable solubility properties may be obtained by reacting formaldehyde or a formaldehyde-yielding reagent with the amine in the presence of reagent B; for example, with a mixture of the amine and an alkyl phenol. The amine and aldehyde may also be reacted in the presence of a mixture of reagents A and B.

The proportions of the various reagents in the mixtures leading to the molybdenum-containing compositions of this invention are not critical but may be adjusted according to the properties desired in the product. Normally, however, about 1–2 equivalents and preferably about 1–1.5 equivalents of component B, and about 0.5–1.5 and preferably about 0.5–1.0 equivalents of component A, are used per equivalent of component C.

In a preferred embodiment of the method of this invention, there is also present in the reaction mixture leading to the molybdenum-containing composition (D) an oil-soluble basic nitrogen-containing dispersant. The amount of dispersant used is generally about 1–10% and preferably about 3–6% by weight, based on the total of components A, B and C; these percentages are exclusive of inert diluents.

The characterizing features of reagent D, with respect to molecular structure, are the presence of at least one basic nitrogen atom and an oil-solubilizing group containing at least about 30 aliphatic carbon atoms bonded directly to a polar group. The dispersant may contain more than one of either of such groups per molecule, as will be apparent from the description hereinafter.

Many of the materials contemplated as reagent D are referred to as "ashless dispersants" although, depending on its constitution, the dispersant may upon combustion yield a non-volatile residue such as boric oxide or phosphorus pentoxide. It does not, however, ordinarily contain metal and therefore does not yield a metal-containing ash on combustion.

Dispersants of this type are known in the art and are described in various patents. Any of such dispersants are suitable for use in preparing the compositions of this invention. The following are illustrative:

(1) Reaction products of carboxylic acids (or derivatives thereof) containing at least about 34 and preferably at least about 54 aliphatic carbon atoms with nitrogen-containing compounds such as amines, ureas and hydrazines. Examples of these products, referred to herein as "carboxylic dispersants", are described in many patents and published applications including U.S. Pat. No. 3,272,746 and German application No. 2,808,105.

(2) Reaction products of aliphatic or alicyclic halides containing at least about 30 carbon atoms with amines, preferably polyalkylene polyamines. These may be characterized as "amine dispersants" and examples thereof are described, for example, in the following U.S. Pat. Nos.:
3,275,554
3,438,757
3,454,555
3,565,804

(3) Reaction products of alkyl phenols in which the alkyl group contains at least about 30 carbon atoms with aliphatic $C \geq 7$ aldehydes (especially formaldehyde) and amines (especially polyalkylene polyamines), which may be characterized as "Mannich dispersants". The materials described in the following U.S. patents are illustrative: U.S. Pat. Nos.
3,413,347
3,697,574
3,725,277
3,725,480
3,726,882

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, sulfur, sulfur halides, boron compounds, phosphorus compounds or the like. Exemplary materials of this kind are described in the following U.S. patents: U.S. Pat. Nos.
3,036,003
3,087,936
3,200,107
3,216,936
3,254,025
3,256,185
3,278,550
3,280,234
3,281,428
3,282,955
3,312,619
3,366,569
3,367,943
3,373,111
3,403,102
3,442,808
3,455,831
3,455,832
3,493,520
3,502,677
3,513,093
3,533,945
3,539,633
3,573,010
3,579,450
3,591,598
3,600,372
3,639,242
3,649,229
3,649,659
3,658,836
3,697,574
3,702,757
3,703,536
3,704,308
3,708,522

The pertinent disclosures of all of the above-noted patents are incorporated by reference herein.

Especially useful as reagent D are dispersants having an average molecular weight no higher than about 5000. Of these, the carboxylic dispersants are preferred. They may be most conveniently and accurately described in terms of radicals I and II present therein. Radical I is usually an acyl, acyloxy or acylimidoyl radical containing at least about 34 carbon atoms. The structures of these radicals, as defined by the International Union of Pure and Applied Chemistry, are as follows (R representing a hydrocarbon or similar group):

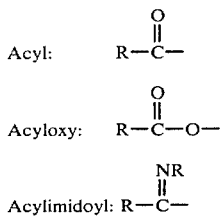

Acyl: R—C(=O)—

Acyloxy: R—C(=O)—O—

Acylimidoyl: R—C(=NR)—

Radical II is preferably at least one radical in which a nitrogen atom is attached directly to said acyl, acyloxy or acylimidoyl radical, said nitrogen atom also being attached to a hydrocarbon-based radical. The nitrogen-containing group therein is derived from compounds characterized by a radical of the structure >NH wherein the two remaining valences of nitrogen are satisfied by hydrogen, amino or organic radicals bonded to said nitrogen atom through direct carbon-to-nitrogen linkages. These compounds include aliphatic, aromatic, heterocyclic and carbocyclic amines as well as substituted ureas, thioureas, hydrazines, quanidines, amidines, amides, thioamides, cyanamides and the like.

Especially preferred as nitrogen-containing compounds used in the preparation of the dispersant are alkylene polyamines and hydroxyalkyl-substituted alkylene polyamines. The alkylene polyamines comprise, in general, alkylene amines containing about 10 or less alkylene groups joined through nitrogen atoms. They include principally the ethylene amines, propylene amines, butylene amines and homologs thereof, and also piperazines and aminoalkyl-substituted piperazines. Hydroxyalkyl-substituted derivatives of these alkylene polyamines are also contemplated for use in preparing the dispersant. Typical examples of suitable amines are ethylene diamine, triethylene tetramine, pentaethylene hexamine, propylene diamine, tripropylene tetramine, di-(trimethylene)triamine, 1,4-bis-(2-aminoethyl)piperazine, 1-(2-aminopropyl)piperazine, N-(2-hydroxyethyl)ethylene diamine, 1-(2-hydroxyethyl)piperazine, and 2-heptadecyl-1-(2-hydroxyethyl)-imidazoline. Also useful are the polyoxyalkylene polyamines (e.g., "Jeffamines"). Mixtures of these amines may also be used.

The preferred amines are the polyethylene polyamines containing from two to about eight amino groups per molecule. A commercially available mixture of polyethylene polyamines containing an average of about 3-7 amino groups per molecule is particularly suitable.

The source of radical I in the dispersant is an acylating agent comprising a carboxylic acid-producing compound containing a hydrocarbon-based substituent which has at least about 30 and preferably at least about 50 aliphatic carbon atoms. By "carboxylic acid-producing compound" is meant an acid, anhydride, acid halide, ester, amide, imide, amidine or the like; the acids and anhydrides are preferred.

The carboxylic acid-producing compound is usually prepared by the reaction (more fully described hereinafter) of a relatively low molecular weight carboxylic acid or derivative thereof with a hydrocarbon source containing at least about 30 and preferably at least about 50 aliphatic carbon atoms. The hydrocarbon source should be substantially saturated, i.e., at least about 95% of the total number of carbon-to-carbon covalent linkages should be saturated. It should also be substantially free from pendant groups containing more than about six aliphatic carbon atoms. It may contain substituents such as those enumerated hereinabove with reference to component C.

The preferred hydrocarbon sources are those derived from substantially saturated petroleum fractions and olefin polymers, particularly polymers of monoolefins having from 2 to about 30 carbon atoms. Thus, the hydrocarbon source may be derived from a polymer of ethylene, propene, 1-butene, isobutene, 1-octene, 3-cyclohexyl-1-butene, 2-butene, 3-pentene or the like. Also useful are interpolymers of olefins such as those illustrated above with other polymerizable olefinic substances such as styrene, chloroprene, isoprene, p-methylstyrene, piperylene and the like. In general, these interpolymers should contain at least about 80%, preferably at least about 95%, on a weight basis of units derived from the aliphatic monoolefins.

Another suitable hydrocarbon source comprises saturated aliphatic hydrocarbons such as highly refined high molecular weight white oils or synthetic alkanes.

In many instances, the hydrocarbon source should contain an activating polar radical to facilitate its reaction with the low molecular weight acid-producing compound. The preferred activating radicals are halogen atoms, especially chlorine, but other suitable radicals include sulfide, disulfide, nitro, mercaptan, ketone and aldehyde groups.

As already pointed out, the hydrocarbon sources generally contain at least about 30 and preferably at least about 50 aliphatic carbon atoms. Among the olefin polymers those having a molecular weight of about 700-5000 are preferred, although higher polymers having molecular weights from about 10,000 to about 100,000 or higher may sometimes be used. (All polymer molecular weights herein are number average molecular weights and are determined by gel permeation chromatography.) Especially suitable as hydrocarbon sources are polybutenes (notably those containing predominantly isobutene units) within the prescribed molecular weight range, and chlorinated derivatives thereof.

Any one of a number of known reactions may be employed for the preparation of the carboxylic acid-producing compound. Thus, an alcohol of the desired molecular weight may be oxidized with potassium permanganate, nitric acid or a similar oxidizing agent; a halogenated olefin polymer may be reacted with a ketene; an ester of an active hydrogen-containing acid, such as acetoacetic acid, may be converted to its sodium derivative and the sodium derivative reacted with a halogenated high molecular weight hydrocarbon such as brominated wax or brominated polyisobutene; a high molecular weight olefin may be ozonized; a methyl ketone of the desired molecular weight may be oxidized by means of the haloform reaction; an organometallic derivative of a halogenated hydrocarbon may be reacted with carbon dioxide; a halogenated hydrocarbon or olefin polymer may be converted to a nitrile, which is subsequently hydrolyzed; or an olefin polymer or its halogenated derivative may undergo a reaction with an unsaturated carboxylic acid or derivative thereof such as acrylic acid, methacrylic acid, maleic acid, maleic anhydride, fumaric acid, itaconic acid, itaconic anhydride, citraconic acid, citraconic anhydride, mesaconic acid, glutaconic acid, chloromaleic acid, aconitic acid, crotonic acid, methylcrotonic acid, sorbic acid, 3-hexenoic acid, 10-decenoic acid, 2-pentene-1,3,5-tricarboxylic acid or the like, or with a halogen-substituted carboxylic acid or derivative thereof. This latter reaction is preferred, especially when the acid-producing compound is unsaturated and preferably when it is maleic acid or anhydride. The resulting product is then a succinic acid or derivative thereof containing a substantially saturated hydrocarbon-based substituent. The reaction leading to its formation involves merely heating the two reactants at about 100°–200° C. The substituted succinic acid or anhydride thus obtained, may, if desired, be converted to the corresponding acid halide by reaction with known halogenating agents such as phosphorus trichloride, phosphorus pentachloride or thionyl chloride.

For the formation of the dispersant, the hydrocarbon-substituted succinic anhydride or acid, or other carboxylic acid-producing compound, and the alkylene polyamine or other nitrogen-containing reagent are heated to a temperature above about 80° C., preferably about 100°–250° C. The product thus obtained has predominantly amide, imide and/or amidine linkages (containing acyl or acylimidoyl groups). The process may in some instances be carried out at a temperature below 80° C. to produce a product having predominantly salt linkages (containing acyloxy groups). The use of a diluent such as mineral oil, benzene, toluene, naphtha or the like is often desirable to facilitate control of the reaction temperature.

The relative proportions of the carboxylic acid-producing compound and the alkylene polyamine or the like are such that at least about one-half the stoichiometrically equivalent amount of polyamine is used for each equivalent of carboxylic acid-producing compound. In this regard it will be noted that the equivalent weight of the alkylene polyamine is based upon the number of amine radicals therein, and the equivalent weight of the carboxylic acid-producing compound is based on the number of acidic or potentially acidic radicals. (Thus, the equivalent weight of a hydrocarbon-substituted succinic acid or anhydride is one-half its molecular weight.) Although a minimum of one-half equivalent of polyamine per equivalent of acylating agent should be used, there does not appear to be an upper limit for the amount of polyamine. If an excess is used, it merely remains in the product unreacted without any apparent adverse effects. Ordinarily, about 1–2 equivalents of polyamine are used per equivalent of acylating agent.

In an alternative method for producing the dispersant, the alkylene polyamine is first reacted with a low molecular weight, unsaturated or halogen-substituted carboxylic acid or derivative thereof (such as maleic anhydride or one of the others previously mentioned) and the resulting intermediate is subsequently reacted with the hydrocarbon source as previously described.

It is possible to prepare the dispersant by reacting the acylating agent simultaneously or, preferably, sequentially with nitrogen-containing compounds and hydroxy reagents. Suitable hydroxy reagents include monohydric alcohols such as methanol, ethanol, isooctanol, dodecanol, cyclohexanol, neopentyl alcohol, monomethyl ester of ethylene glycol and the like, or polyhydric alcohols such as ethylene glycol, diethylene glycol, dipropylene glycol, tetramethylene glycol, pentaerythritol, glycerol and the like. Carbohydrates (e.g., sugars, starches, cellulose) are also suitable as are partially esterified derivatives of polyhydric alcohols having at least three hydroxy radicals. Aliphatic polyols containing up to 10 carbon atoms and at least 3 hydroxy groups, especially those with up to 6 carbon atoms and 3–6 hydroxy groups, are preferred.

The relative amounts of the nitrogen-containing compound and hydroxy reagent may be between about 10:1 and 1:10, on an equivalent weight basis. The methods of preparation of these dispersants are generally the same as for those previously described, except that two sources of radical II are used. Mixtures of independently prepared dispersants are also suitable.

Typical carboxylic dispersants suitable for use as reagent D are listed in Table I. "Reagent I" and "Reagent II" are, respectively, the sources of radicals I and II as previously defined.

TABLE I

| Example | Reagent I | Reagent II | Ratio of equivalents, I:II | Reaction temperature, °C. | Diluent (percent by weight in parentheses) |
|---|---|---|---|---|---|
| 5 | Polyisobutenyl (mol. wt. about 900) succinic anhydride prepared from chlorinated polyisobutene | Polyethylene amine mixture containing about 3–7 amino groups per molecule | 0.48 | 150 | Mineral oil (40) |
| 6 | Same as Example 5 | Pentaethylene hexamine | 0.41 | 150 | Mineral oil |
| 7 | Like Example 5 except polyisobutene mol. wt. is about 1050 | Pentaethylene hexamine | 0.61 | 150 | Mineral oil |
| 8 | Like Example 5 except polyisobutene mol. wt. is about 850 | Diethylene triamine | 1.0 | 150 | Mineral oil |
| 9 | Same as Example 8 | Ethylene diamine | 1.0 | 150 | Mineral oil |
| 10 | Same as Example 8 | Di-(1,2-propylene)triamine | 1.0 | 180–190 | Mineral oil-toluene |
| 11 | Same as Example 8 | N-(2-Hydroxyethyl)-trimethylene diamine | 1.06 | 150–155 | Mineral oil |
| 12 | Same as Example 5 | Pentaerythritol, followed by polyethylene amine of Example 5 (ratio of equivalents 3.4:1) | 0.79 | 205–215 | Mineral oil (45) |
| 13 | Same as Example 5 | Same as Example 5 | 0.67 | 150 | Mineral oil (40) |
| 14 | Same as Example 5 | Same as Example 5 | 1.33 | 150 | Mineral oil (40) |
| 15 | Like Example 5 except polyisobutene mol. wt. is about | Pentaerythritol, followed by polyethylene amine of Example 5 (ratio of | 0.44 | 150–210 | Mineral oil (45) |

TABLE I-continued

| Example | Reagent I | Reagent II | Ratio of equivalents, I:II | Reaction temperature, °C. | Diluent (percent by weight in parentheses) |
|---|---|---|---|---|---|
| | 1100 | equivalents 7.7:1) | | | |
| 16 | Acid produced by reaction of chlorinated (3.6% Cl) polyisobutene (mol. wt. 750) with KCN, followed by hydrolysis | Ethylene diamine | 2.0 | 150 | Xylene |
| 17 | Methyl ester produced by reaction of chlorinated (4.7% Cl) polyisobutene (mol. wt. 1000) with methyl methacrylate | Triethylene tetramine | 1.0 | 140–220 | — |
| 18 | Reaction product of sodiomalonic ester with $C_{75}$ brominated wax | Same as Example 5 | 0.4 | 150 | Xylene |
| 19 | Reaction product of chlorinated (4.5% Cl) polyisobutene (mol. wt. 850) with acrylic acid | Pentaethylene hexamine | 0.8 | 180–200 | — |
| 20 | Acid produced by haloform reaction with methyl heptacontanyl ketone | Same as Example 5 | 0.8 | 180–210 | — |
| 21 | Same as Example 5 | Same as Example 5 | 1.0 | 150 | Mineral oil (43) |

The preparation of the molybdenum-containing compositions of this invention is illustrated by the following examples. All parts and percentages are by weight.

EXAMPLE 22

A mixture of 592 parts (1 equivalent) of the product of Example 1, 254 parts (1.2 equivalents) of heptylphenol, 300 parts of toluene and 100 parts of water is heated to 50° C. and 206 parts (1 equivalent) of ammonium paramolybdate is added. The mixture is heated under reflux for 1 hour as water is removed by azeotropic distillation. A portion of the toluene is removed and 200 parts of mineral oil and 56 parts of the product of Example 21 are added. The solution is filtered using a filter aid material and the remaining volatiles are stripped under vacuum. The residue is a 67% solution in oil of the desired product; it contains 5.74% molybdenum.

EXAMPLE 23

A mixture of 592 parts (1 equivalent) of the product of Example 1, 254 parts (1.32 equivalents) of heptylphenol, 200 parts of mineral oil, 60 parts of the product of Example 21, 150 parts of water and 200 parts of toluene is heated to 60° C. Ammonium paramolybdate, 206 parts (1 equivalent), is added and the mixture is heated under reflux for 2 hours. It is then vacuum stripped and filtered to yield the desired product as a 70% solution in mineral oil, containing 6.74% molybdenum.

EXAMPLE 24

A mixture of 354 parts (1 mole) of "Duomeen T", 266 parts (1 mole) of tetrapropene-alkylated phenol, 150 parts of mineral oil and 200 parts of toluene is heated to 70° C. and 66 parts (2 moles) of paraformaldehyde is added. The mixture is heated under reflux for 3 hours as water is removed by azeotropic distillation. It is then stripped by blowing with nitrogen while heating to 170° C. The residue is filtered using a filter aid material.

A mixture of 415 parts (1 equivalent) of the "Duomeen T"-paraformaldehyde condensation product, 342 parts of mineral oil, 42 parts of the product of Example 21, 250 parts of toluene and 150 parts of water is heated to 60° C. and 177 parts (0.86 equivalent) of ammonium paramolybdate is added. The mixture is heated under reflux for 3 hours and is then vacuum stripped while blowing with nitrogen. Upon filtration, the desired product is obtained as a 56% solution in mineral oil; it contains 6.49% molybdenum.

Also contemplated as part of this invention are combinations of the above-described molybdenum-containing compositions with at least one compound containing active sulfur. As used herein, the term "active sulfur" refers to chemically combined sulfur which has the effect of staining copper under the conditions of the Copper Strip Tarnish Test (ASTM Procedure D130). In the compositions of this invention which include active sulfur compounds, the weight ratio of the molybdenum-containing composition to the active sulfur compound is generally about 0.3–3.0:1.

Suitable active sulfur compounds are known to those skilled in the lubricant art. They include the following:

Sulfurized olefinic compounds, prepared by the reaction of sulfur, a sulfur halide, combinations of hydrogen sulfide and sulfur dioxide, or the like with such compounds as isobutene, 1-hexene, 1-octene, 1-dodecene, polybutenes, alkyl cyclohexenecarboxylates, glycerides and the like.

Sulfurized mercaptans, prepared by the reaction of the sulfurizing agents enumerated above with mercaptans corresponding to the listed olefinic compounds.

Sulfurized phenolic compounds, prepared by the reaction of the sulfurizing agents enumerated above with phenol, alkyl phenols, Mannich reaction products of alkyl phenols with formaldehyde and amines, and the like.

Dialkyl xanthates and carbamates.

As previously indicated, the compositions of this invention are useful as additives for lubricants, in which they function primarily as extreme pressure and friction modifying agents. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes), etc. and mixtures thereof]; alkylbenzenes [e.g., dodecylbenzenes, tetradecylbenzenes, dinonylbenzenes, di-(2-ethylhexyl)benzenes, etc.]; polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants [e.g., tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)-disiloxane, poly(methyl)-siloxanes, poly(methylphenyl)siloxanes, etc.]. Other synthetic lubricating oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants of the present invention contain an amount of the composition of this invention sufficient to provide it with improved extreme pressure and frictional properties. Normally this amount will be about 0.05–10.0 parts by weight, preferably about 0.1–5.0 parts, per 100 parts of lubricant.

The invention also contemplates the use in lubricants of other additives in combination with the molybdenum-containing compositions (and, optionally, active sulfur compounds). Such additives include, for example, detergents and dispersants of the ash-producing or ashless type, corrosion- and oxidation-inhibiting agents, pour point depressing agents, auxiliary extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-β-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are described hereinabove with reference to component D.

Auxiliary extreme pressure agents and corrosion- and oxidation-inhibiting agents are exemplified by chlorinated aliphatic hydrocarbons such as chlorinated wax; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Illustrative lubricant compositions of this invention are listed in Table II. All amounts therein, except those for mineral oil and the products of Examples 22 and 24, are exclusive of mineral oil used as diluent.

TABLE II

| Ingredient | Lubricant | Parts by weight | |
| --- | --- | --- | --- |
| | | A | B |
| Mineral oil | | 84.32 | 84.98 |
| Product of Example 22 | | 2.00 | — |
| Product of Example 24 | | — | 1.20 |
| Sulfurized alkyl cyclohexene-carboxylate | | 1.30 | 1.32 |
| Pentaerythritol ester of polybutenyl (mol. wt. about 1000) succinic acid | | 3.48 | 3.51 |
| Polybutenyl (mol. wt. about 1000) succinic anhydride-ethylene polyamine (containing an average of 3–7 nitrogen atoms) reaction mixture | | 0.11 | 0.11 |
| Isodecyl acrylate polymer | | 8.34 | 8.42 |
| Hindered phenol antioxidant | | 0.45 | 0.46 |
| Silicone anti-foam agent | | 0.006 | 0.006 |

The molybdenum-containing compositions of this invention which are free of sulfur compounds may also be used as fuel additives to decrease friction and fuel consumption. The resulting fuel compositions, which constitute another embodiment of the invention, contain a major proportion of a normally liquid fuel, usually a hydrocarbonaceous petroleum distillate fuel such as motor gasoline as defined by ASTM Specification D439 or diesel fuel or fuel oil as defined by ASTM Specification D396. Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and methanol or ethanol and diesel fuel and ether. Particularly preferred is gasoline, that is, a mixture of hydrocarbons having an ASTM boiling point from about 60° C. at the 10% distillation point to about 205° C. at the 90% distillation point.

Generally, these fuel compositions contain about 1–50,000, preferably about 4–10,000, parts by weight of the molybdenum-containing composition per million parts of fuel.

The fuel compositions can obtain, in addition to the molybdenum-containing composition of this invention, other additives which are well known to those of skill in the art. These can include antiknock agents such as tetraalkyl lead compounds, lead scavengers such as halo-alkanes (e.g., ethylene dichloride and ethylene dibromide), deposit preventors or modifiers such as triaryl phosphates, dyes, cetane improvers, antioxidants such as 2,6-di-tertiarybutyl-4-methylphenol, rust inhibitors such as alkylated succinic acids and anhydrides, bacteriostatic agents, gum inhibitors, metal deactivators, demulsifiers, upper cylinder lubricants, anti-icing agents and the like.

The compositions of this invention can be added directly to the fuel or lubricant. Preferably, however, they are diluted with a substantially inert, normally liquid organic diluent such as mineral oil, naphtha, benzene, toluene or xylene, to form an additive concentrate. These concentrates usually contain about 20–90% by weight of the molybdenum-containing composition of this invention and may contain, in addition, one or more other additives known in the art or described hereinabove.

What is claimed is:

1. A method for preparing a molybdenum-containing composition substantially free of Group IA and IIA metals which comprises reacting, at a temperature up to about 200° C., a mixture comprising (A) at least one acid of molybdenum, or salt thereof; (B) at least one phenol, or condensation product of said phenol with at least one lower aldehyde; and (C) at least one compound selected from the group consisting of (1) amines having the formula $$R^3-NH-R^4-NH_2$$
$$|$$
$$R^2$$

wherein $R^2$ is hydrogen or an aliphatic hydrocarbon-based radical, $R^3$ is an aliphatic hydrocarbon radical free from acetylenic unsaturation and containing at least about 6 carbon atoms, and $R^4$ is a divalent aliphatic hydrocarbon radical containing about 2–8 carbon atoms; (2) condensation products of said amines with at least one lower aldehyde; and (3) salts of (1) or (2).

2. A method according to claim 1 wherein reagent B is at least one alkyl phenol in which the alkyl group contains about 3–100 carbon atoms.

3. A method according to claim 2 wherein $R^2$ is hydrogen.

4. A method according to claim 2 wherein reagent A is at least one ammonium molybdate.

5. A method according to claim 4 wherein reagent C is a condensation product of said amines with formaldehyde or a formaldehyde-yielding reagent, $R^3$ contains about 12–22 carbon atoms, and $R^4$ is a $C_{2-4}$ alkylene radical.

6. A method according to claim 5 wherein $R^3$ contains 16–18 carbon atoms and $R^4$ is the trimethylene radical.

7. A method according to claim 2 wherein reagent C is prepared in situ by the reaction of said amine with formaldehyde or a formaldehyde-yielding reagent in the presence of reagent B or of a mixture of reagents A and B.

8. A method according to claim 2 wherein there is also present (D) at least one oil-soluble basic nitrogen-containing dispersant.

9. A method according to claim 8 wherein reagent D is at least one carboxylic dispersant characterized by the presence within its molecular structure of an acyl, acyloxy or acylimidoyl radical containing at least about 34 carbon atoms and a radical in which a nitrogen atom is attached directly to said acyl, acyloxy or acylimidoyl radical, said nitrogen atom also being attached to an aliphatic hydrocarbon-based radical.

10. A method according to claim 9 wherein reagent D is prepared by the reaction of a succinic acid or anhydride containing a substantially saturated hydrocarbon-based substituent with at least one of an alcohol and an alkylene polyamine.

11. A method according to claim 10 wherein the hydrocarbon-based substituent on the succinic acid or anhydride contains at least about 50 aliphatic carbon atoms.

12. A method for preparing a molybdenum-containing composition of matter which comprises reacting, at a temperature up to about 200° C., a mixture comprising (A) at least one ammonium molybdate; (B) at least one alkyl phenol wherein the alkyl group contains 6–20 carbon atoms; (C) at least one condensation product of formaldehyde and N-tallow-substituted trimethylene diamine; and (D) a basic dispersant prepared by the reaction of at least one succinic acid or derivative thereof containing a substantially saturated hydrocarbon-based substituent having at least about 50 aliphatic carbon atoms with at least one ethylene polyamine.

13. A method according to claim 12 wherein reagent A is ammonium paramolybdate.

14. A molybdenum-containing composition prepared by the method of claim 1, 2, 3, 5, 6, 7, 10 or 12.

15. A composition comprising a molybdenum-containing composition according to claim 14 and at least one compound containing active sulfur.

16. An additive concentrate comprising a substantially inert, normally liquid organic diluent and about 20–90% by weight of a composition according to claim 14.

17. An additive concentrate comprising a substantially inert, normally liquid organic diluent and about 20–90% by weight of a composition according to claim 15.

18. A lubricating composition comprising a major amount of a lubricating oil and a minor amount of a composition according to claim 14.

19. A lubricating composition comprising a major amount of a lubricating oil and a minor amount of a composition according to claim 15.

20. A fuel composition comprising a major amount of a normally liquid fuel and a minor amount of a composition according to claim 14.

21. A fuel composition comprising a major amount of a normally liquid fuel and a minor amount of a composition according to claim 15.

* * * * *